(12) United States Patent
Lux

(10) Patent No.: US 12,102,440 B1
(45) Date of Patent: Oct. 1, 2024

(54) METHOD AND SYSTEM FOR MEASURING CARDIAC ELECTROGRAM DEPOLARIZATION VOLTAGE

(71) Applicant: Neucures Inc., Los Angeles, CA (US)

(72) Inventor: Robert L. Lux, Park City, UT (US)

(73) Assignee: NEUTRACE INC., Longwood, FL (US)

( * ) Notice: Subject to any disclaimer, the term of this patent is extended or adjusted under 35 U.S.C. 154(b) by 144 days.

(21) Appl. No.: 17/073,239

(22) Filed: Oct. 16, 2020

(51) Int. Cl.
*A61B 5/349* (2021.01)
*A61B 5/308* (2021.01)
*A61B 5/339* (2021.01)

(52) U.S. Cl.
CPC ............. *A61B 5/349* (2021.01); *A61B 5/308* (2021.01); *A61B 5/339* (2021.01)

(58) Field of Classification Search
CPC .... A61N 1/36507; A61N 1/365; A61N 1/371; A61B 5/367; A61B 5/339; A61B 5/349; A61B 5/352; A61B 5/366
See application file for complete search history.

(56) References Cited

U.S. PATENT DOCUMENTS

| | | | |
|---|---|---|---|
| 9,538,929 B2 * | 1/2017 | Yang | A61B 5/0044 |
| 2019/0328258 A1 * | 10/2019 | Gaeta | A61B 5/061 |
| 2022/0142553 A1 * | 5/2022 | Markovitz | A61B 5/367 |

* cited by examiner

*Primary Examiner* — George R Evanisko
(74) *Attorney, Agent, or Firm* — Caldwell Intellectual Property Law

(57) ABSTRACT

A system and a method for determining cardiac tissue health based on a depolarization wave within an electrogram (EGM) is disclosed. The method comprises selecting a portion of the depolarization wave demarcated by a start time and end time and computing a Peak-to-Peak (P2P) voltage for the electrogram by computing a difference in voltages of the EGM corresponding to the start time and the end time.

9 Claims, 12 Drawing Sheets

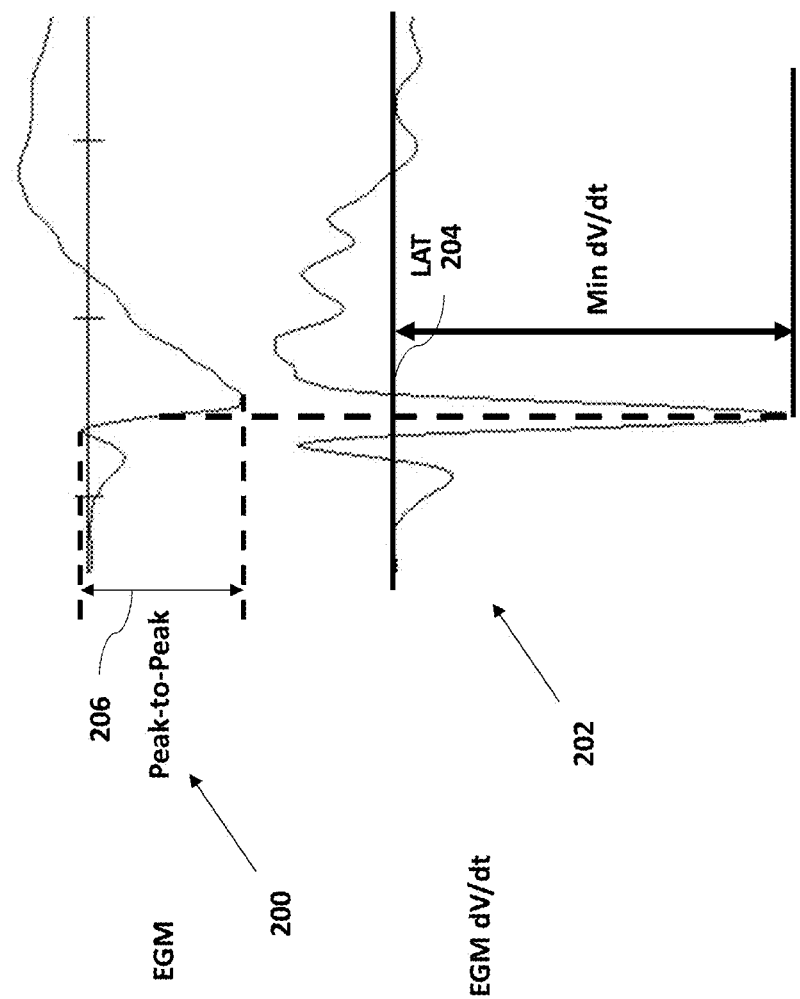
FIG. 2a. Determining Peak-to-Peak Voltage

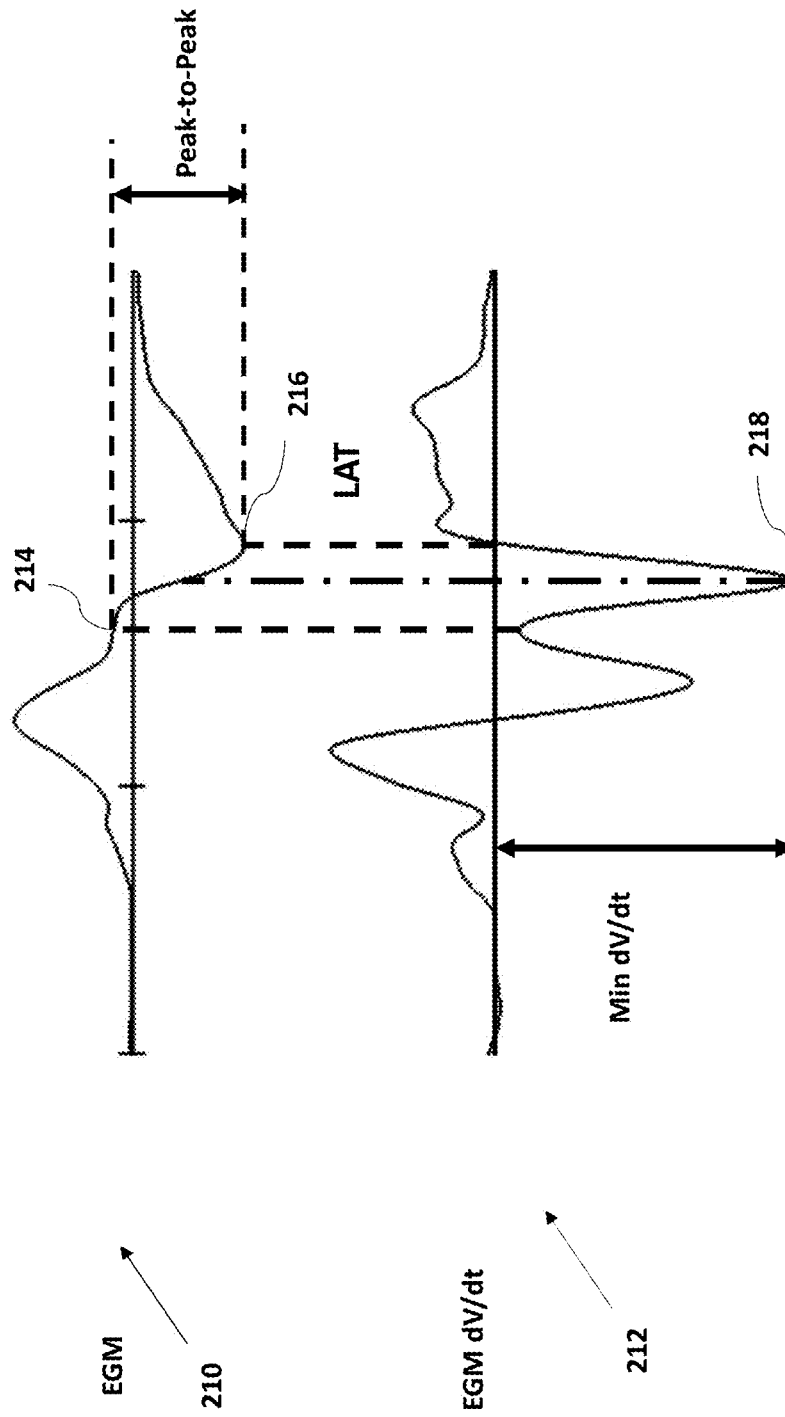

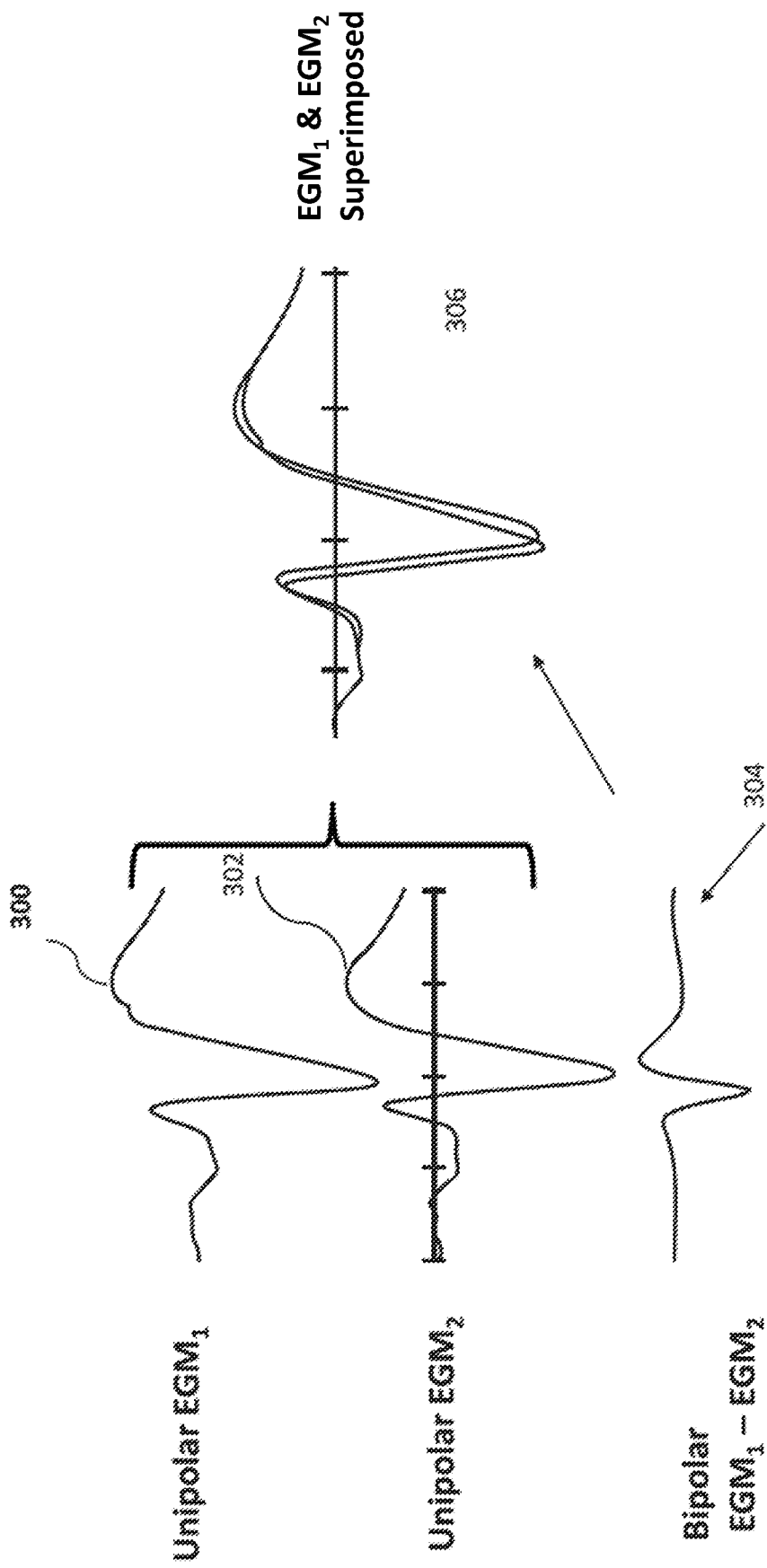
FIG 3. Constructing Bipolar EGM from two Unipolar EGMs

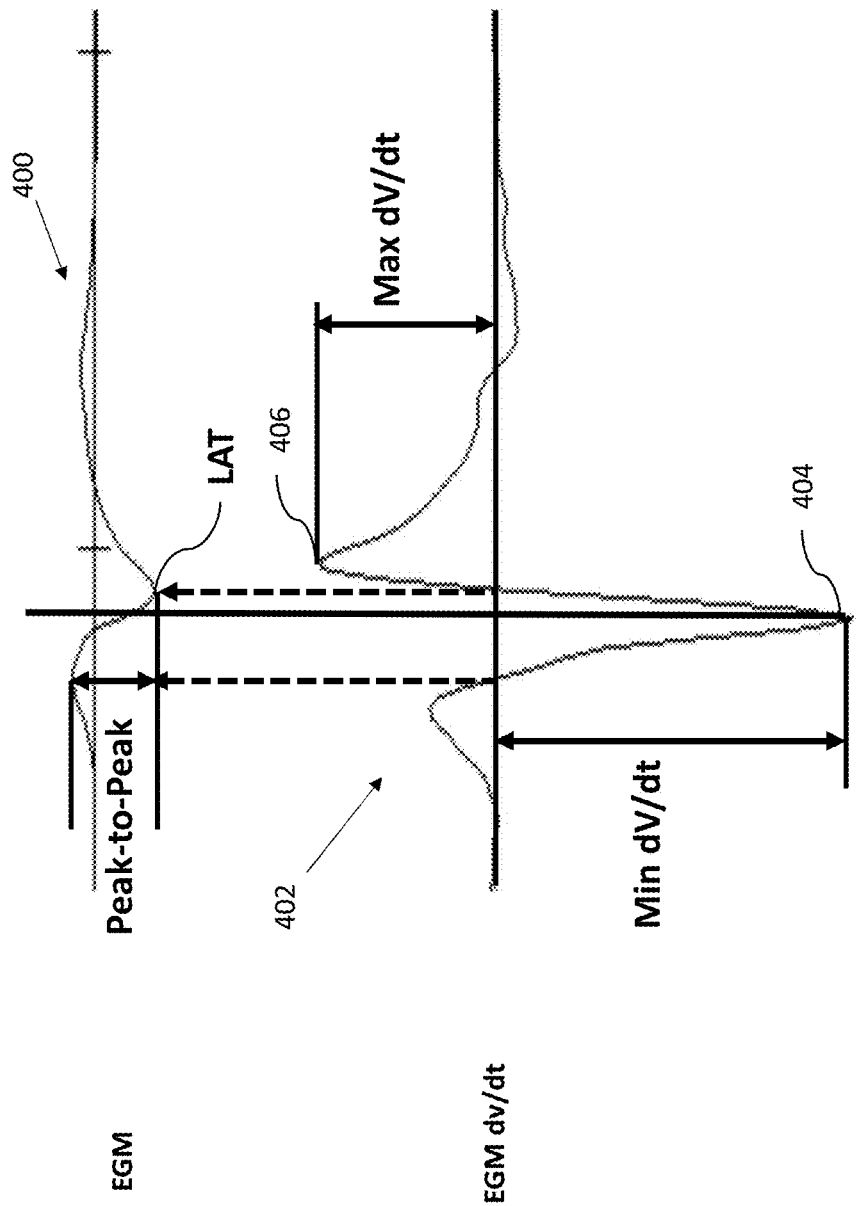

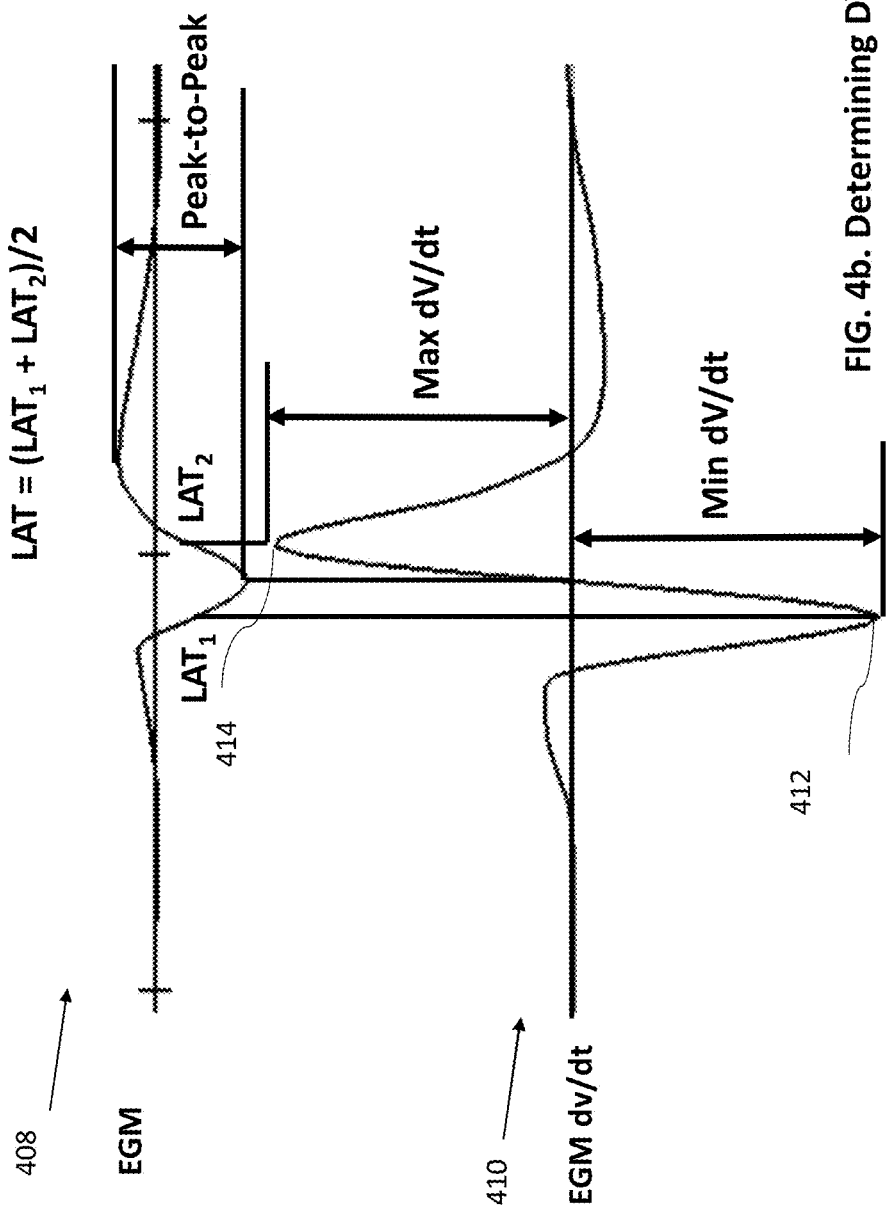

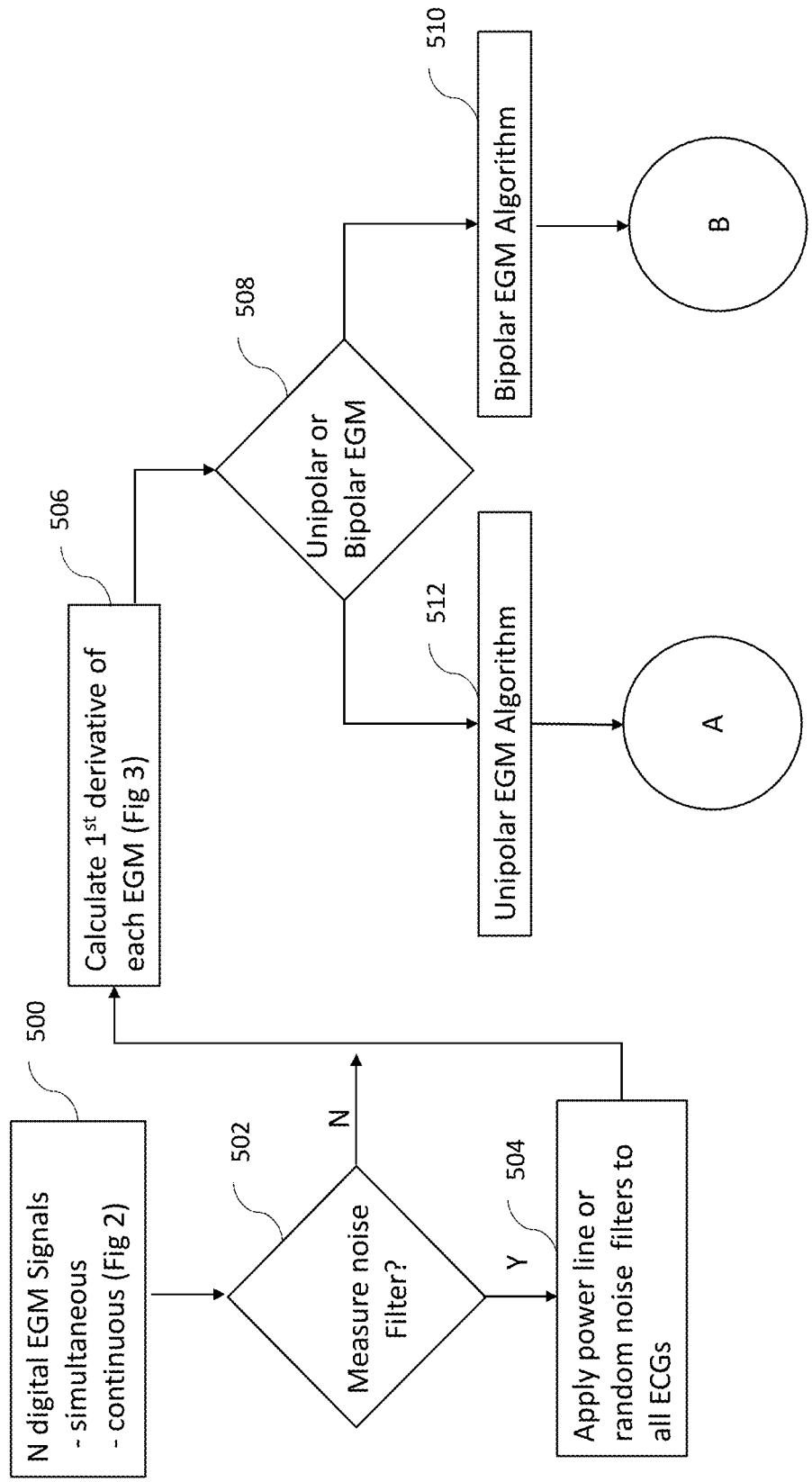
FIG 5a: A Flow Chart for Determining $DV/DT_{MIW}$

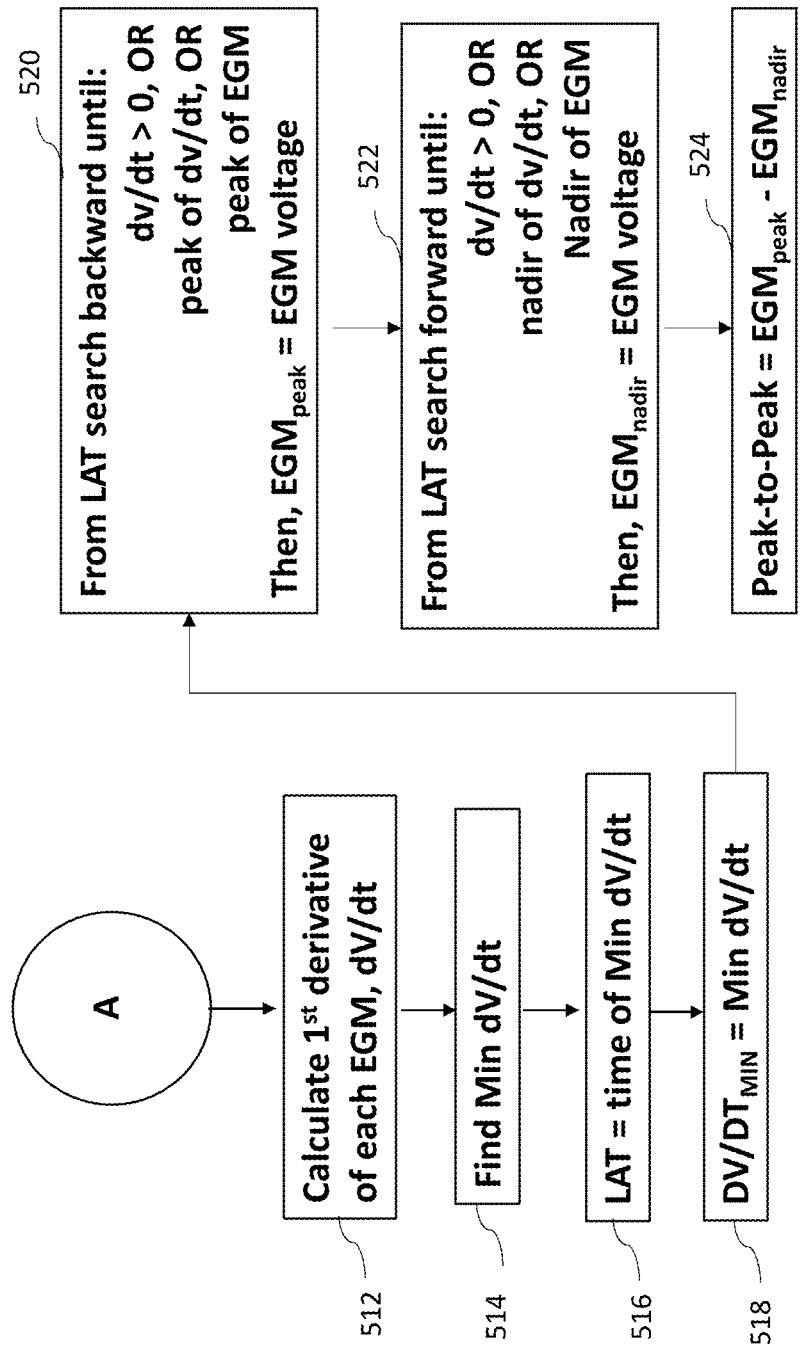
FIG 5b: Flow Chart for Determining Unipolar $DV/DT_{MIN}$

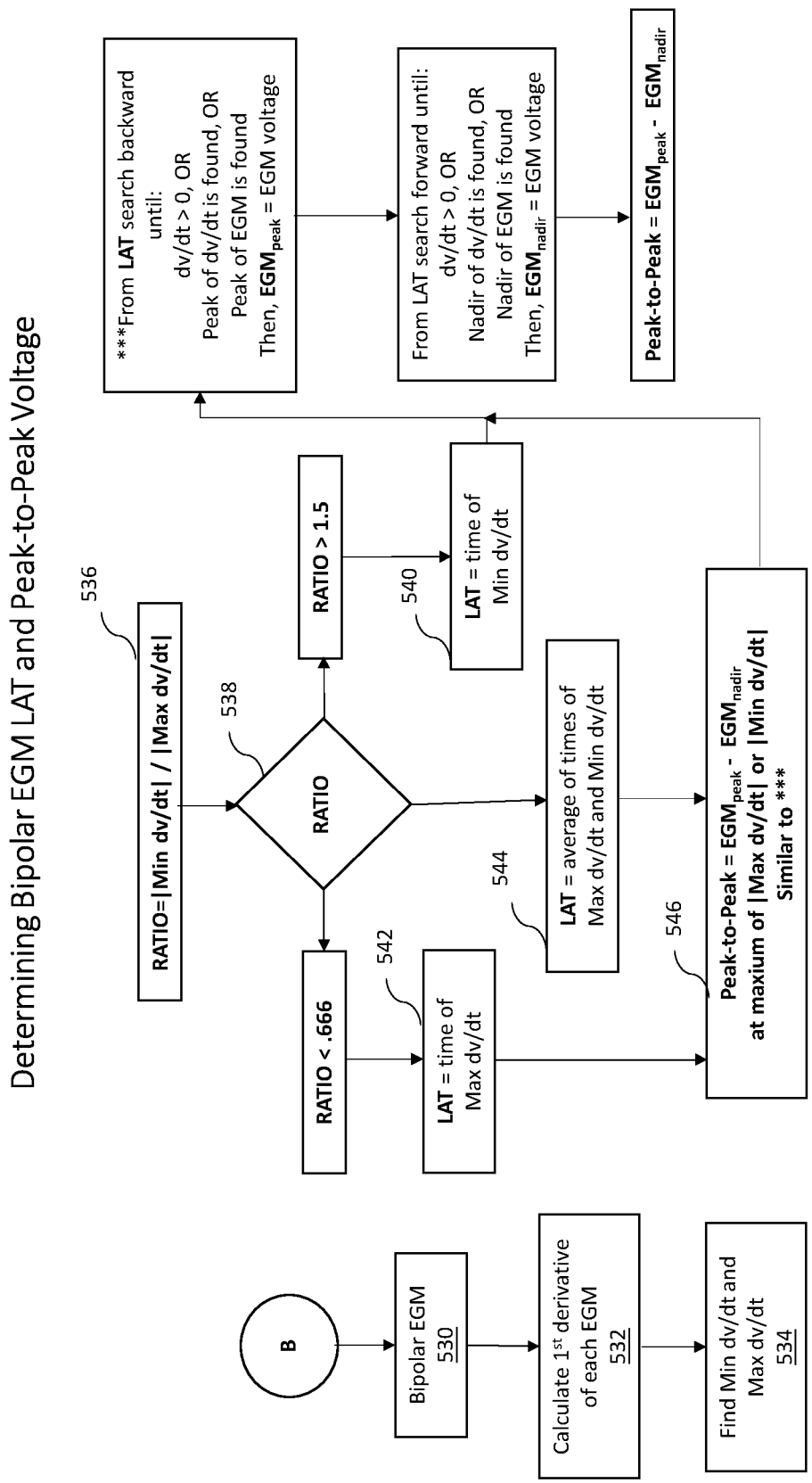
FIG 5c : Flow Chart for Determining Bipolar LAT and Peak-to-Peak Voltage

METHOD AND SYSTEM FOR MEASURING CARDIAC ELECTROGRAM DEPOLARIZATION VOLTAGE

FIELD

Embodiments of the present invention relate to systems and methods for quantitating and characterizing a plurality of signals from the heart.

BACKGROUND

Electrical activity generated by the heart can be measured by arrays of electrodes placed on and within the cardiac muscle. The recorded tracings are called electrograms (EGMs). The dominant wave of EGMs, the depolarization wave, reflects the electrical depolarization (excitation) of the heart that leads to its contraction.

The depolarization wave of each EGM contains information about the health of the tissue near the electrode and quantitative measurements of the wave provide a means to separate normal and abnormal cardiac tissue. Aspects of the depolarization wave relate specifically to the heart tissue local to the electrodes.

SUMMARY

Broadly, embodiments of the present invention disclose techniques for accurately determining an amplitude of the voltage associated with a depolarization wave within each electrogram. Said amplitude is measured between two adjacent infection points in the depolarization wave and is referred to as the Peak-to-Peak (P2P) voltage. In one embodiment, the method for calculating the P2P voltage comprises the following steps:
  determining the first derivative of the depolarization wave;
  determining the Local Activation Time (LAT) from the first derivative;
  detecting the times of the first inflections (change of slope magnitude and/or polarity) before and after the LAT; and
  calculating the voltage difference between the two inflection points of the EGM, (the P2P voltage) based on separate rules for unipolar (one pole electrode) and bipolar (two pole electrode) EGMs.

Other aspects of the invention will be apparent from the written description below.

BRIEF DESCRIPTION OF THE DRAWINGS

FIGS. 2a & 2b show examples of unipolar EGMs and their first derivatives with respect to time and illustrates aspects of the computation of LAT and P2P voltage in accordance with one embodiment of the invention.

FIG. 3 shows an example of a construction of a bipolar EGM from two closely spaced unipolar EGMs, in accordance with one embodiment of the invention.

FIGS. 4a & 4b show examples of bipolar EGMs and their first derivatives with respect to time an illustrates aspects of aspects of how LAT and P2P voltage may be computed for the dominant and nondominant cases, in accordance with one embodiment of the invention.

FIGS. 5a-5c show flowcharts of techniques for computing P2P voltage from unipolar and bipolar EGMs, in accordance with one embodiment of the invention.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Figure 1:
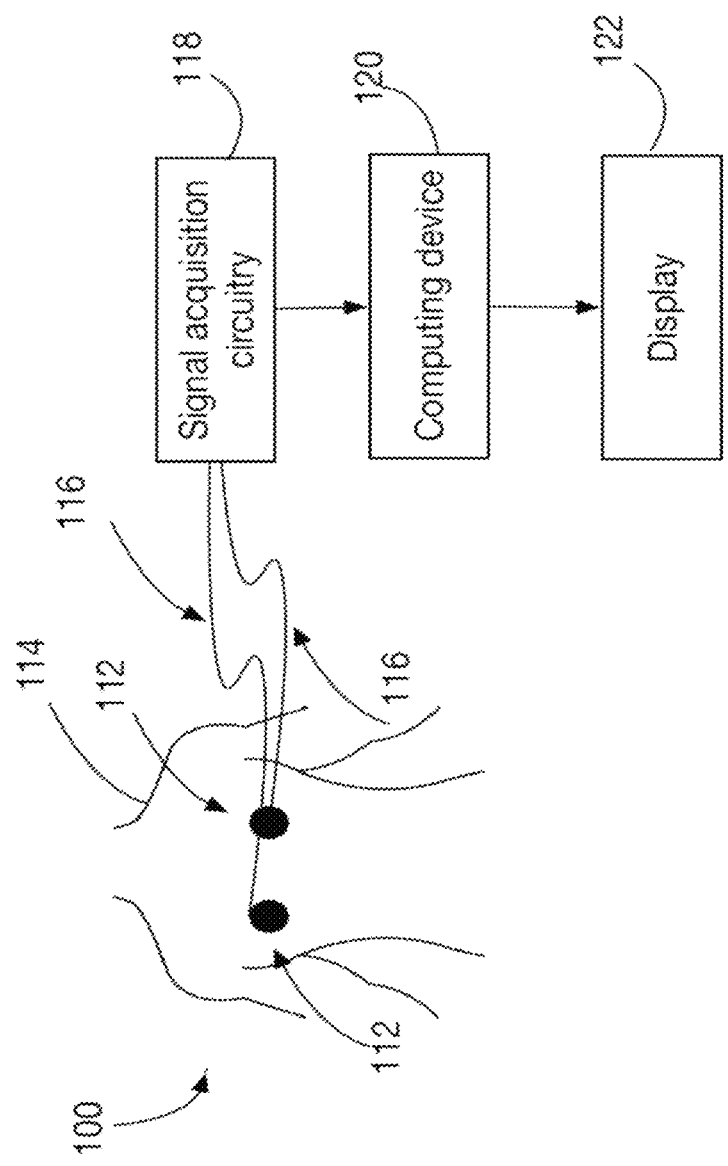
FIG. 1 shows an exemplary system for acquiring cardiac signals in accordance with one embodiment of the invention.

FIG. 1 of the drawings shows an exemplary system 100 for acquiring cardiac signals in accordance with one embodiment of the invention. As will be seen, the system 100 comprises a plurality of electrodes 112 that that may be positioned on the torso of a patient 114. The electrodes 112 may be configured to measure body-surface potentials (electrocardiograms or ECGs) of the patient 114, e.g. the torso-surface potentials of a patient 114. Additional electrodes on catheters inserted into the heart cavity or on the heart surfaces collect signals called electrograms (EGMs) Each electrode signal (body surface or heart) is coupled via an electrical lead 116 to interface/amplifier circuitry 118.

The interface/amplifier circuitry 118 may be configured to amplify the signals from the electrodes 112 and provide the signals to a computing device 120. In other embodiments, a wireless connection may be used to transmit the signals sensed by electrodes 112 to the interface/amplifier circuitry 118 and, in turn, the computing device 120, e.g., as channels of data. For example, the interface/amplifier circuitry 118 may be electrically coupled to each of the computing device 120 using, e.g., analog electrical connections, digital electrical connections, wireless connections, bus-based connections, network-based connections, internet-based connections, etc. The computing device 120 may be operatively coupled to a display device 122 for displaying information to an operator.

The device 120 may record and analyze the torso-surface potential signals sensed by electrodes 112 and amplified/conditioned by the interface/amplifier circuitry 118. The computing device 120 may be configured to analyze the signals from the electrodes 112 to provide electrical activation information or data such as cardiac electrical activation times, e.g., representative of actual, or local, electrical activation times of one or more regions of the patient's heart as will be further described herein.

Additionally, the computing device 120 may be configured to provide graphical user interfaces depicting the electrical activation times obtained using the electrodes 112 on the display device 122.

EGMs represent the voltage signals which show a rapid change at the time of a heartbeat that corresponds to the propagating electrical wave that initiates contraction of the heart. Embodiments of the present invention disclosed techniques to measure the P2P voltage of the depolarization wave in each EGM. The figures show graphically how the measurements are made.

Referring now to FIG. 2a of the drawings, reference 200 generally indicates a unipolar EGM, whereas reference numeral 202 indicates its first derivative DV/DT with respect to time. Local activation time (LAT) corresponds to the time at which the first derivative DV/DT with respect to time is at a minimum (nadir), which point is depicted by reference numeral 204. It is to be noted that the EGM 200 is characterized by a sharp down stroke in the signal which corresponds to the LAT point 204. A peak-to peak value 206 is determined based on detecting inflections in the EGM wave 200 using the DV/DT wave 202 at times immediately before and after the detected LAT time 204 as will be described.

FIG. 2b of the drawings shows another example of a unipolar EGM indicated generally by reference numeral 210. In this case, the EGM 210 has an inflection point 214 in its down stroke and reaches a minimum 216. Reference 212 generally indicates the first derivative with respect to time (DV/DT) of the EGM 210. For this case, the minimum point 218 in the DV/DT corresponding to that portion of the down slope in the EGM 210 between the inflection point 214 and the minimum point 216 is taken to be the minimum value for DV/DT. The time of the minimum point 218 is taken to be the time for LAT. A peak-to-peak value is determined based on detecting inflections in the EGM wave 210 using the DV/DT wave 212 at times immediately before and after the detected LAT time (the LAT corresponds to the time of the minimum point 218) as will be described.

FIG. 3 shows how a bipolar EGM can be constructed from two unipolar EGMs received from two closely spaced unipolar electrodes. Referring to FIG. 3, reference numerals 300 and 302 generally indicate two closely spaced EGMs, respectively. To calculate the bipolar EGM 304, the EGM 302 is subtracted from the EGM 300. Reference numeral 306 depicts a superimposition of the EGMs 300 and 302. Order of subtraction (polarity of the EGM) is immaterial).

FIG. 4a show an example of a bipolar EGM 400 and its first derivative with respect to time (DV/DT) 402. As will be seen, the first derivative with respect to time 402 comprises two extrema. The extrema include a minima 404 and a maxima 406. It will be seen that the minima 404 is much greater in magnitude than the maxima 406. For this case, the Local Activation Time (LAT) is set as the time of the derivative's minimum magnitude, |Min dv/dt|, which as noted above is much greater than the derivative's maximum value, |Max dv/dt|. Thus, the bipolar EGM 402 represents a dominant case Peak-to-Peak voltage is calculated as the difference between inflection points on either side of the LAT FIG. 4b shows an example of a bipolar EGM 408 and its first derivative with respect to time (DV/DT) 410. The first derivative with respect to time 410 includes a minima 412, and a maxima 414. As will be seen, the values for the minima 412 and maxima 414 are similar and thus no one value is dominant over the other. Hence, the EGM 408 is referred to as the nondominant case. For this case, Local Activation Time (LAT) may be set as the average of the times at which the derivative with respect to time is minimum in magnitude, |Min dv/dt| and the derivative is maximum (|Max dv/dt|) in magnitude. In this case, and in accordance with the embodiment of invention, $DV/DT_{MIN}$ may be the same as the Min dV/dt (negative by nature) or the negative of Max dV/dt, –Max dV/dt, as will be explained in detail in flowcharts in FIG. 5 and FIG. 6. Peak-to-Peak voltage is determined as the difference between the maximum and minimum EGM voltages on either side of the maximum (dV/dt|.

FIGS. 5a to 5c, show a flowchart of operations performed to calculate P2P voltage in accordance with one embodiment of the invention. Referring to FIG. 5a at block 500, N digital ECG signals may be simultaneously and continuously acquired from the unit 118. Processing block 502 may measure the noise level in the signals, and determine if the noise level is above a certain threshold in which case control passes to block 504 wherein noise reduction techniques are performed to remove or at least reduce the noise levels. Various techniques may be employed to remove noise detected in the signals. For example, power line or random noise filters may be applied to all ECGs.

Once the N ECG signals with appropriate noise levels are obtained, processing may be transitioned to block 506, wherein the first derivative of each EGM is computed. At block 508, a determination is made to distinguish the EGMs as bipolar or unipolar. For unipolar EGMs, control process to block 512 (see FIG. 5b), and for bipolar EGMs, control passes to block 510 (see FIG. 5c).

Referring to FIG. 5b, block 512 the first derivative with respect to time for each EGM is calculated. At block 514, the minima Min dV/dt in the first derivative is located. LAT is said to be the time at which the minima Min dV/dt occurs (block 516) and $DV/DT_{MIN}$ is set to Min dV/dt. Once the LAT time is determined control passes to block 520 where a search is performed in the signals (that is the EGM and its first derivative with respect to time) prior to the LAT time in order to check if any of the following conditions are true: i) if dv/dt>0, or ii) if there is a peak in the first derivative dv/dt, or iii) there is a peak in the EGM. In one embodiment, the value of the EGM wave at the time before the LAT time when any of the above mentioned three conditions becomes true is determined to be the $EGM_{peak}$ voltage.

At block 522, an $EGM_{nadir}$ voltage is determined by performing a search after the LAT time to check if any of the following conditions are true: i) dv/dt>0, or ii) if there is a nadir in the first derivative dv/dt, or iii) there is a nadir in the EGM. In one embodiment, the value of the EGM wave at the time after the LAT time when any of the above mentioned three conditions becomes true is determined to be the $EGM_{nadir}$ voltage. At block 524, a peak-to-peak value is determined by subtracting $EGM_{nadir}$ value from $EGM_{peak}$ value.

Advantageously, the P2P values thus computed may be used to evaluate cardiac tissue. In particular, higher values for P2P voltage may be indicative of normal or healthy tissue, whereas lower values may be indicative of abnormal or unhealthy tissue.

As will be understood by one of ordinary skill in the art, the first derivative of the signals may be computed according to the following equation:

Equation for calculating the EGM derivative, dv/dt:
Least Mean Squared Error (LSME) Parabolic Fit of Data $$j\dot{E}GM_k = A \sum_{i=1}^{n} i(jEGM_{k+i} - jEGM_{k-i})$$

where j EGM is the $j^{th}$ EGM, k is the sample time, and A is dependent on n.

FIG. 5c of the drawings shows a flowchart of operations performed to determine the peak-to-peak voltage value, in accordance with one embodiment of the invention. As will be seen, at block 530, a bipolar EGM signal is received and at block 532, a first derivative with respect to time of the bipolar EGM signal is calculated. At block 534, Min dv/dt values and Max dv/dt values are determined as illustrated in FIGS. 4a and 4b. At block, 536, a ratio |Min dv/dt|/|Max dv/dt| is determined. At block 538, if the ratio is determined to be greater than 1.5, the LAT time is determined to be the time at which the Min dv/dt value occurs at block 540. In case, at block 538 the ratio is determined to be less than 0.666, the LAT time is determined to be the time at which the Max dv/dt value occurs at block 542. In case, at block 538 the ratio is determined to be between 0.666 and 1.5, the LAT time is determined to be an average of the time at which the Min dv/dt value occurs and the time at which the Max dv/dt value occurs in block 544. Once the LAT time is determined a value for $EGM_{peak}$ and $EGM_{nadir}$ value is determined as per the steps described in FIG. 5b. At block, 546, a peak-to-peak voltage value in the EMG signal is determined by subtracting the EGM nadir value from $EGM_{peak}$ value.

Figure 6:
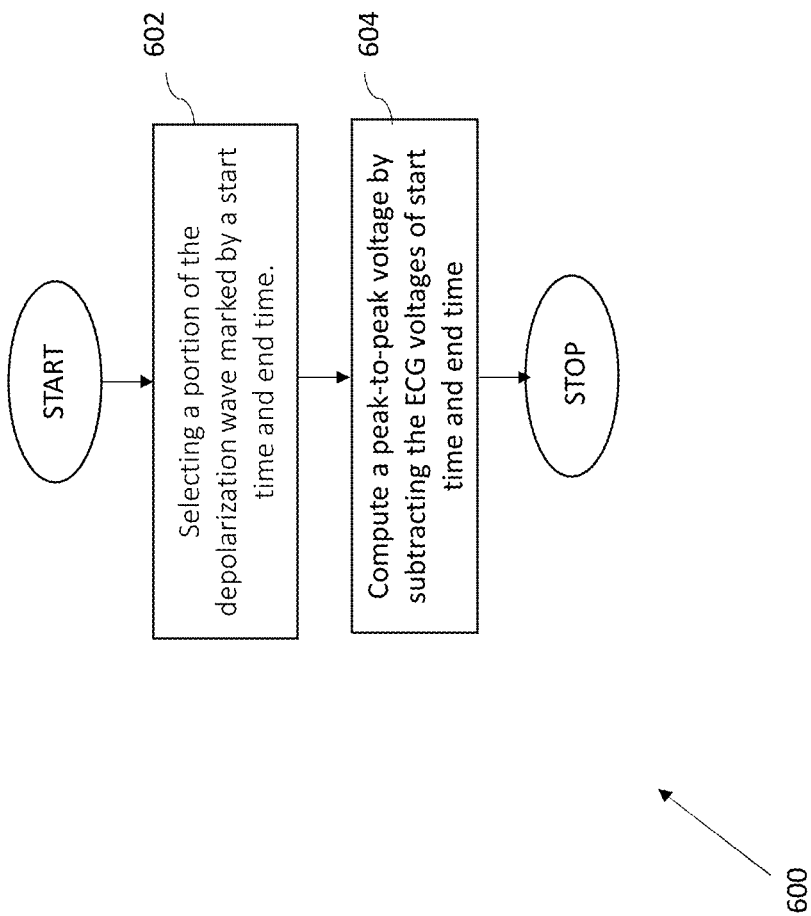
FIG. 6 shows a flowchart of key steps of the techniques illustrated and described with respect to FIGS. 5a-5c, in accordance with one embodiment of the invention.

FIG. 6 shows a flowchart of key steps of the techniques illustrated and described with respect FIGS. 5a-5c, in accordance with one embodiment of the invention.

Referring to FIG. 6, at block 602, a portion of the depolarization wave is selected, wherein said portion is demarcated by a start time, and an end time.

At block 604 a Peak-to-Peak (P2P) voltage for the electrogram is computed by computing a difference in voltages of the EGM corresponding to the start time and the end time.

Selecting the portion of the depolarization wave may be based on Local Activation Time (LAT).

Selecting the portion of the depolarization wave may comprise searching backwards relative to the LAT to determine the start time; and searching forwards relative to the LAT to determine the end time.

The backwards search is conducted until any one of the following conditions is met: a first derivative with respect to time DV/DT of the electrogram is greater than zero, there is a peak in said first derivative, and there is a peak in the electrogram itself, whereupon said start time is set to be the time at which any one of said conditions is first met.

The forward search may be conducted until any one of the following conditions is met: the first derivative with respect to time DV/DT of the electrogram is greater than zero, there is a nadir in said first derivative, and there is a nadir in the electrogram itself, whereupon said end time is set to be the time at which any one of said conditions is first met.

The techniques disclosed herein may be used with systems that include graphical user interfaces for use by users to evaluate a patient's cardiac health and/or adjust cardiac therapy. As described herein with reference to FIG. 1, the exemplary systems and methods described herein may use display apparatus 122 including a graphical user interface. The graphical user interface may be configured to, among other things, present information for use in assisting a user in evaluating a cardiac a patient's cardiac health. For example, the graphical user interface may be configured to display Local Activation Times and values for P2P voltage. Further, for example, the graphical user interface may be configured to display a spatial map of electrical activation times and values for Min dV/dt.

Advantageously, the techniques disclosed herein for computing P2P voltage, unlike clinical methods that utilize a voltage range across the entire depolarization wave for the computation of the P2P voltage which are disadvantageous because said voltage range includes voltage generated by currents arising far from the measurement EGM site within the heart, is based on a very narrow search window of the depolarization wave and is thus more representative of the local electrical activity within the heart.

Figure 7:
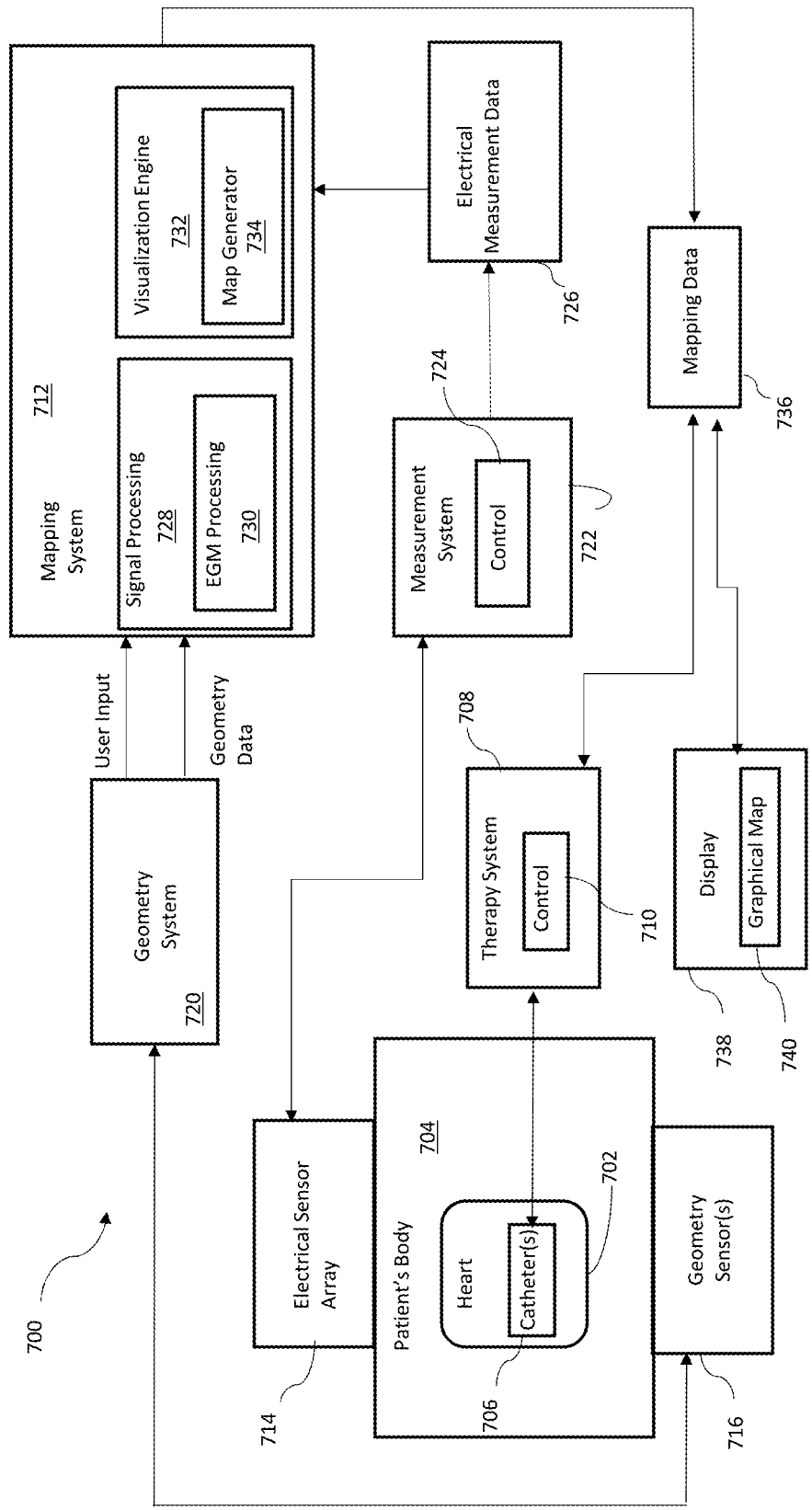
FIG. 7 of the drawings shows an exemplary diagnostic/treatment system, in accordance with one embodiment of the invention.

FIG. 7 of the drawings shows an exemplary diagnostic/treatment system 700, in accordance with one embodiment of the invention. The system 700 is capable of assessing the condition of the heart 702 in real-time as part of a treatment or diagnostic procedure. For this purpose, the system 700 includes one or more catheters that can be inserted into a patient's body 704 thereby to contact the patient's heart 702—more specifically the endocardium or the epicardium. One of ordinary skill in the art would understand and appreciate that various types and configurations of catheters 706 may be utilized, depending on the type of treatment and procedure.

In some cases, the therapy system 706 may include one or more electrodes located at the tip of an ablation catheter which in use is configured to ablate tissue in response to electrical signals (for example radiofrequency energy) supplied by a therapy system 708. In other cases, the therapy delivery device 706 may include one or more electrodes located at the tip of a pacing catheter to deliver electrical stimulation for pacing the heart in response The therapy system 708 may be located external to the patient's body 704 and may be configured to control the type of therapy that is delivered by the device 706. For example, the therapy system 708 may include control circuitry 710 configured to deliver electrical signals by a conductive link electrically connected between the device (electrodes) 706 and the therapy system 708. The control circuitry 710 may provide control parameters for the signals supplied to the device 706 (these may include current, voltage, etc.) For delivering therapy (example ablation) via the electrode (s) 704 to one or more sites within the heart 702, the control circuitry 710 may set therapy parameters and apply stimulation based on automatic, manual (user input) or a combination of automatic and manual mechanisms. In some embodiments, one or more sensors (not shown) may be configured to communicate since the information back to the therapy system 708. The position of the catheter 706 within the heart 702 may be determined and tracked by a mapping system 702. Location of the device 706 and in the therapy parameters may be combined to provide corresponding therapy parameters data.

In some embodiments, prior to providing therapy by the therapy system 708 and other system or subsystem may be utilized to acquire electrophysiological data for the patient. For this purpose, a sensor array 714 including one or more electrodes may be utilized for recording patient activity. In some cases, the sensor array 714 may include an arrangement of body surface sensors distributed over a portion of the patient's torso for measuring electrical activity associated with the patient's heart. The catheter 706 may include one or more electrodes that can be utilized in conjunction with the sensor array 714 for mapping electrical activity of the endocardial surface such as the wall of the heart chamber. Additionally, such electrodes may be used to obtain location or positional information of the catheter 706 within the heart which can advantageously be used to register electrical information of the heart in an image or map is generated by the system 700. In some embodiments, to facilitate the tracking of the catheter 706 positional within the heart, geometry sensors 716 may be positioned around the patient's body and configured to sense the position of the catheter 706 within the heart. For example, in some embodiments, the catheter 706 may be comprise with a magnetic element that can be sensed by the geometry sensors 716 to the to derive catheter positional data that is transmitted to a geometry system 720. The geometry system 720 may be configured to generate geometry data which is then input into the mapping systems 712.

In one embodiment, the sensor array 714 may be configured to provide the sensed electrical information to a corresponding measurement system 722. The measurement system 722 may include control circuitry 724 and signal processing circuitry (not shown) for generating electrical measurement data 726 that describes electrical activity detected by sensors in the sensor array 714. The electrical measurement data 726 may comprise analog and/or digital information. In some embodiments, the control circuitry 724 may be configured to control a data acquisition process for measuring electrical activity of the heart and generating the electrical measurement data 726. The electrical measurement data 726 may be acquired concurrently with the therapy delivered by the therapy system 708.

The mapping system 712 may be configured to combine the electrical measurement data 726 with geometry data generated by the geometry system 720 by applying appropriate processing computations. For example, the mapping system 712 may include a single processing module 728 configured to process the signals generated by the geometry system 720 and measurements system 722. For example, the signal processing module 728 may include an EGM processing module 730 configured to process EGM signals associated with the heart in accordance with the techniques described above including calculating P2P voltage. A visualize relation engine 732 of the mapping systems and 712 may be provisioned with a mapped generator function 734 configured to render various metrics associated with the heart in visual form. For this purpose, the visualization engine 732 outputs mapping data 736 that can be rendered on a display 738 as a graphical map 740 showing various metrics associated with the heart.

By way of example, the geometry data output but the geometry system 720 may comprise a graphical representation of the patient's torso in the form of image data acquired for the patient. In one embodiment, the geometry system 720 may process the image data to extract and segment anatomical features of the heart. Additionally, positional information for the sensors within the electrical sensor array 714 may be included in the geometry data. The geometry data may be converted into a two-dimensional or three-dimensional graphical representation that includes regions of interest within the patient's heart by the mapping systems 712.

In other embodiments, the geometry data may include a mathematical model of the patient's heart instructed based on image data for the patient. Anatomical or other landmarks, including locations for the electrodes within the sensor array 714 may be identified in the geometry data to facilitate registration of the electrical measurement data 726. Identification of said landmarks may be performed manually based on the user input, or automatically by means of image processing techniques.

The mapped generator 734 may be configured to generate activation maps for the patient's heart, showing various metrics such as electrical activation times, and indications for QRS onset, the DV/DT, fractionation, etc.

In some embodiments, the system 100 acquiring cardiac signals described above may be embedded within the system 700.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware, such as shown and described with respect to the computer system of FIG. 8.

Figure 8:
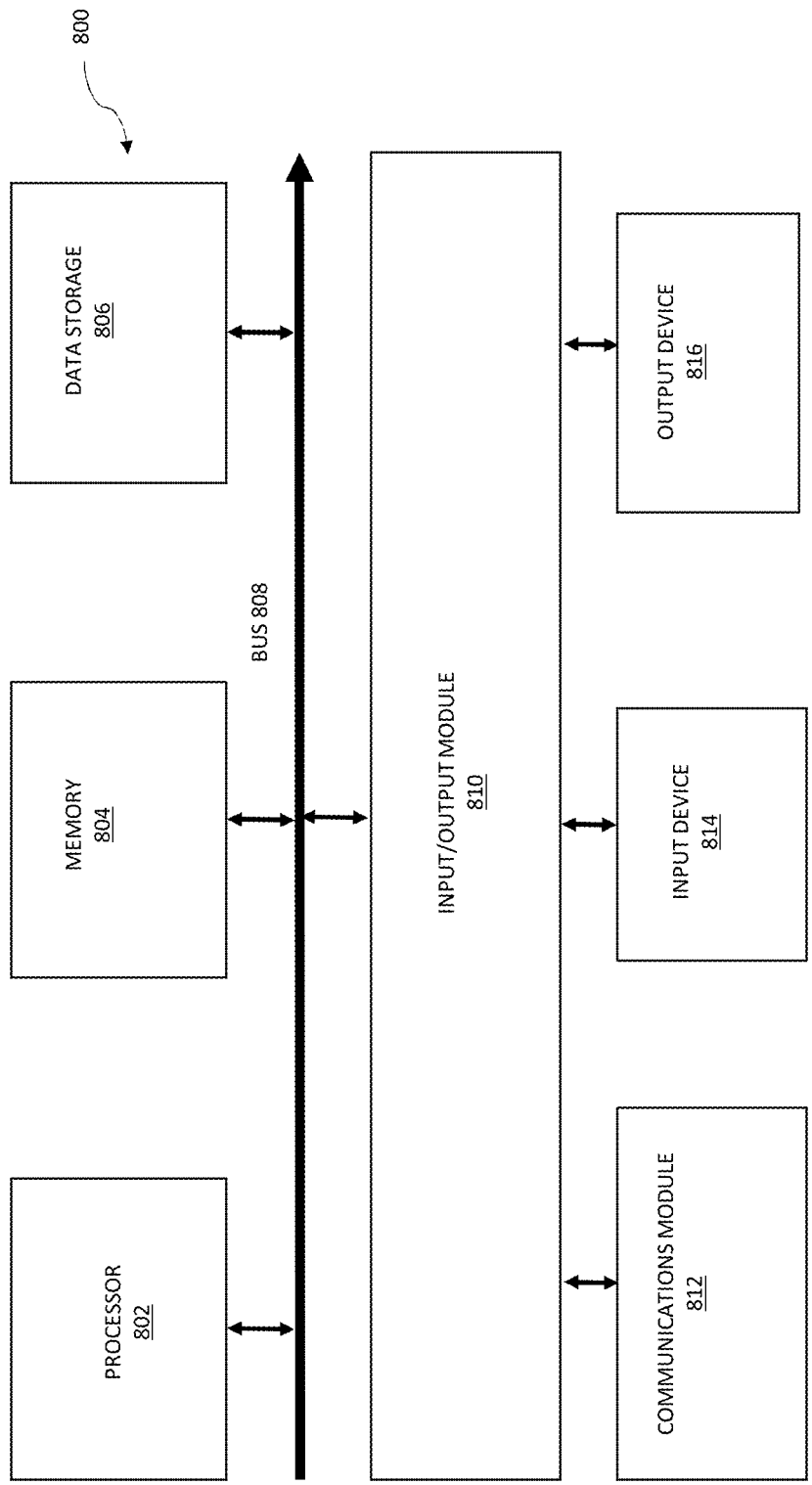
FIG. 8 shows a high-level block diagram of hardware that may be used to practice aspects of the present invention.

FIG. 8 is a block diagram illustrating exemplary hardware for executing some of the techniques disclosed herein, in accordance with one embodiment of the invention. In certain aspects, the computer system 800 may be implemented using hardware or a combination of software and hardware, either in a dedicated server or integrated into another entity or distributed across multiple entities.

Computer system 800 (e.g., client or server) includes a bus 808 or other communication mechanism for communicating information, and a processor 802 coupled with bus 808 for processing information. According to one aspect, the computer system 800 may be implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 800 may be implemented with one or more processors 802.

Processor 802 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 800 can include, in addition to hardware, code that creates an execution environment for the computer program in question, e.g., code that constitutes processor firmware, a protocol stack, a database management system, an operating system, or a combination of one or more of them stored in an included memory 804 such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 808 for storing information and instructions to be executed by processor 802. The processor 802 and the memory 804 can be supplemented by, or incorporated in, special purpose logic circuitry. Expansion memory may also be provided and connected to computer system 800 through input/output module 810, which may include, for example, a SIMM (Single in Line Memory Module) card interface. Such expansion memory may provide extra storage space for computer system 800 or may also store applications or other information for computer system 800. Specifically, expansion memory may include instructions to carry out or supplement the processes described above and may include secure information also. Thus, for example, expansion memory may be provided as a security module for computer system 800 and may be programmed with instructions that permit secure use of computer system 800. In addition, secure applications may be provided via the SIMM cards, along with additional information, such as placing identifying information on the SIMM card in a non-hackable manner.

The instructions may be stored in the memory 804 and implemented in one or more computer program products, i.e., one or more modules of computer program instructions encoded on a computer readable medium for execution by, or to control the operation of, the computer system 800, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 804 may also be used for storing temporary variable or other intermediate information during execution of instructions to be executed by processor 802.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 870 further includes a data storage device 806 such as a magnetic disk or optical disk, coupled to bus 808 for storing information and instructions. Computer system 800 may be coupled via input/output module 810 to various devices. The input/output module 810 can be any input/output module. Example input/output modules 810 include data ports such as USB ports. In addition, input/output module 810 may be provided in communication with processor 802, so as to enable near area communication of computer system 800 with other devices. The input/output module 810 may provide, for example, for wired communication in some implementations, or for wireless communication in other implementations, and multiple interfaces may also be used. The input/output module 810 is configured to connect to a communications module 812. Example communications modules 812 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 812 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 812 sends and receives electrical, electromagnetic or optical signals that carry digital data streams representing various types of information. The network link typically provides data communication through one or more networks to other data devices. For example, the network link of the communications module 812 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 812, which carry the digital data to and from computer system 800, are example forms of transmission media.

Computer system 800 can send messages and receive data, including program code, through the network(s), the network link and communications module 812. In the Internet example, a server might transmit a requested code for an application program through Internet, the ISP, the local network and communications module 810. The received code may be executed by processor 802 as it is received, and/or stored in data storage 806 for later execution.

In certain aspects, the input/output module 810 is configured to connect to a plurality of devices, such as an input device 812 (e.g., input device 814) and/or an output device 814 (e.g., output device 814). Example input devices 812 include a stylus, a finger, a keyboard and a pointing device, e.g., a mouse or a trackball, by which a user can provide input to the computer system 800. Other kinds of input devices 812 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 814 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 814 may comprise appropriate circuitry for driving the output device 814 to present graphical and other information to a user.

According to one aspect of the present disclosure, the techniques disclosed here in may be implemented on the computer system 800 in response to processor 802 executing one or more sequences of one or more instructions contained in memory 804. Such instructions may be read into memory 804 from another machine-readable medium, such as data storage device 806. Execution of the sequences of instructions contained in main memory 804 causes processor 802 to perform the process steps described herein. One or more processors in a multi-processing arrangement may also be employed to execute the sequences of instructions contained in memory 804. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 800 can include clients and servers. A client and server are generally remote from each other and typically interact through a communication network. The relationship of client and server arises by virtue of computer programs running on the respective computers and having a client-server relationship to each other. Computer system 800 can be, for example, and without limitation, a desktop computer, laptop computer, or tablet computer. Computer system 800 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 802 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 806. Volatile media include dynamic memory, such as memory 804. Transmission media include coaxial cables, copper wire, and fiber optics, including the wires that comprise bus 808. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 808. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The invention claimed is:

1. A method for determining cardiac tissue health based on a depolarization wave within an electrogram (EGM), comprising:
   sensing the EGM of a user;
   extracting a portion of the depolarization wave from the sensed EGM;
   determining, a local activation time (LAT); wherein determining the LAT further comprises:

determining a minimum DV/DT value and a maximum DV/DT value;
calculating a ratio of the magnitude of the minimum DV/DT value divided by the maximum DV/DT value;
determining if the value of the ratio is greater than 1.5, less than 0.666, or in between 0.666 and 1.5; and
determining the LAT based at least on the value of the ratio;
determining a start time of the depolarization wave by searching backwards relative to the LAT;
determining an end time of the depolarization wave by searching forward relative to the LAT;
computing a Peak-to-Peak (P2P) voltage for the sensed EGM by computing a difference in voltages of the EGM at the start time and the end time; and
displaying the computed P2P voltage and the determined LAT on a display device for determining the cardiac tissue health of the user.

2. The method of claim 1, wherein said backwards search comprises:
searching for a first peak in said first derivative DV/DT;
searching for a second peak in the EGM itself until any one of the following conditions is met:
the first derivative with respect to time DV/DT of the EGM is greater than zero, presence of the first peak in said first derivative, and
presence of the second peak in the EGM itself, and
setting said start time as the time at which any one of said conditions is first met.

3. The method of claim 1, wherein said forward search comprises:
searching for a first peak in said first derivative DV/DT;
searching for a second peak in the EGM itself until any one of the following conditions is met:
the first derivative with respect to time DV/DT of the EGM is greater than zero, presence of a nadir in said first derivative, and
presence of the nadir in the EGM itself; and
setting said end time as the time at which any one of said conditions is first met.

4. A system for determining cardiac tissue health based on a depolarization wave within an electrogram (EGM), comprising:
a signal acquisition module to sense the EGM of a user;
a display device;
one or more processors coupled to a memory programmed with executable instructions to: extract a portion of the depolarization wave from the sensed EGM;
determine, a local activation time (LAT); wherein determining the LAT further comprises:
determining a minimum DV/DT value and a maximum DV/DT value;
calculating a ratio of the magnitude of the minimum DV/DT value divided by the maximum DV/DT value;
determining if the value of the ratio is greater than 1.5, less than 0.666, or in between 0.666 and 1.5; and
determining the LAT based at least on the value of the ratio;
determine a start time of the depolarization wave by searching backwards relative to the LAT;
determine an end time of the depolarization wave by searching forward relative to the LAT;
determine a mechanism to compute a Peak-to-Peak (P2P) voltage for the EGM by computing a difference in voltages of the EGM corresponding to the start time and the end time; and
control the display device to display the computed P2P voltage and the determined LAT to determine the cardiac tissue health of the user.

5. The system of claim 4, wherein said backwards search is conducted by said one or more processors until any one of the following conditions is met:
the first derivative with respect to time DV/DT of the EGM is greater than zero,
presence of a first peak in said first derivative, and
presence of a second peak in the EGM itself,
wherein said start time is set by said one or more processors to be the time at which any one of said conditions is first met.

6. The system of claim 4, wherein said forward search is conducted until any one of the following conditions is met:
the first derivative with respect to time DV/DT of the EGM is greater than zero,
presence of a first nadir in said first derivative, and
presence of a second nadir in the EGM itself, and
wherein said end time is set to be the time at which any one of said conditions is first met.

7. A non-transitory computer readable storage medium, having stored thereon, a set of computed-executable instructions that causes a computer to perform the steps comprising:
sensing an electrogram (EGM) of a user;
extracting a portion of depolarization wave from the sensed EGM;
determining, a local activation time (LAT); wherein determining the LAT further comprises:
determining a minimum DV/DT value and a maximum DV/DT value;
calculating a ratio of the magnitude of the minimum DV/DT value divided by the maximum DV/DT value;
determining if the value of the ratio is greater than 1.5, less than 0.666, or in between 0.666 and 1.5; and
determining the LAT based at least on the value of the ratio;
determining a start time of the depolarization wave by searching backwards relative to the LAT;
determining an end time of the depolarization wave by searching forward relative to the LAT;
computing a Peak-to-Peak (P2P) voltage for the EGM by computing a difference in voltages of the EGM corresponding to the start time and the end time; and
displaying the computed P2P voltage and the determined LAT on a display device for determining the cardiac tissue health of the user.

8. The non-transitory computer readable storage medium of claim 7, wherein said backwards search is conducted until any one of the following conditions is met:
the first derivative with respect to time DV/DT of the EGM is greater than zero,
presence of a first peak in said first derivative, and
presence of a second peak in the EGM itself,
wherein said start time is set by said one or more processors to be the time at which any one of said conditions is first met.

9. The non-transitory computer readable storage medium of claim 7,
wherein said forward search is conducted until any one of the following conditions is met:

the first derivative with respect to time DV/DT of the
   EGM is greater than zero, presence of a first nadir in
   said first derivative, and
presence of a second nadir in the EGM itself, and
wherein said end time is set to be the time at which any
   one of said conditions is first met.

\* \* \* \* \*